(12) United States Patent  (10) Patent No.: US 8,747,461 B2
Centola  (45) Date of Patent: Jun. 10, 2014

(54) CARDIAC VALVE PROSTHESIS SYSTEM

(75) Inventor: Marcos Centola, Sao Paulo (BR)

(73) Assignee: NVT AG, Muri AG (CH)

( * ) Notice: Subject to any disclaimer, the term of this patent is extended or adjusted under 35 U.S.C. 154(b) by 239 days.

(21) Appl. No.: 12/980,087

(22) Filed: Dec. 28, 2010

(65) Prior Publication Data

US 2011/0125258 A1    May 26, 2011

Related U.S. Application Data

(63) Continuation of application No. PCT/EP2008/005868, filed on Jul. 17, 2008.

(51) Int. Cl.
*A61F 2/24*    (2006.01)
(52) U.S. Cl.
USPC .......................................... 623/2.19; 623/1.26
(58) Field of Classification Search
CPC ....... A61F 2/24; A61F 2/2409; A61F 2/2418; A61F 2/2475
USPC .............. 623/1.24, 1.26, 2.1–2.19, 2.38–2.41
See application file for complete search history.

(56) References Cited

U.S. PATENT DOCUMENTS

| | | | |
|---|---|---|---|
| 6,299,637 B1 * | 10/2001 | Shaolian et al. | 623/1.24 |
| 6,368,345 B1 * | 4/2002 | Dehdashtian et al. | 623/1.13 |
| 6,652,578 B2 | 11/2003 | Bailey | |
| 2003/0236568 A1 | 12/2003 | Hojeibane | |
| 2004/0186558 A1 * | 9/2004 | Pavcnik et al. | 623/1.24 |
| 2005/0075730 A1 * | 4/2005 | Myers et al. | 623/2.18 |
| 2006/0217794 A1 | 9/2006 | Ruiz | |
| 2006/0241745 A1 | 10/2006 | Solem | |
| 2007/0061002 A1 | 3/2007 | Paul, Jr. | |
| 2007/0078510 A1 | 4/2007 | Ryan | |
| 2007/0282436 A1 | 12/2007 | Pinchuk | |
| 2010/0168839 A1 * | 7/2010 | Braido et al. | 623/1.26 |

FOREIGN PATENT DOCUMENTS

| | | |
|---|---|---|
| DE | 10065824.5 | 12/2000 |
| EP | 0 592 410 | 4/1994 |

* cited by examiner

*Primary Examiner* — David Isabella
*Assistant Examiner* — Suba Ganesan
(74) *Attorney, Agent, or Firm* — Casimir Jones SC

(57) ABSTRACT

The present invention concerns a cardiac valve prosthesis system (10; 40) for implantation into the body of a mammal. The prosthesis system (19; 40) comprises a valve (16) mounted on an stent element (18) to form a stented valve element (12), and an anchoring element (14) to be arranged within the aorta of the mammal to be treated with the prosthesis and spaced-apart form the stented valve element (12). Further, the anchoring element (14) comprises a cylindrical tube element composed of fabric (22) supported by a metal mesh, and the stented valve element (12) and the anchoring element (14) represent two constructional distinctive elements being associated by ligament-like connecting means (30; 50), such, that the connecting region (28) between the stented valve element (12) and the anchoring element (14) is generally free from foreign material.

15 Claims, 3 Drawing Sheets

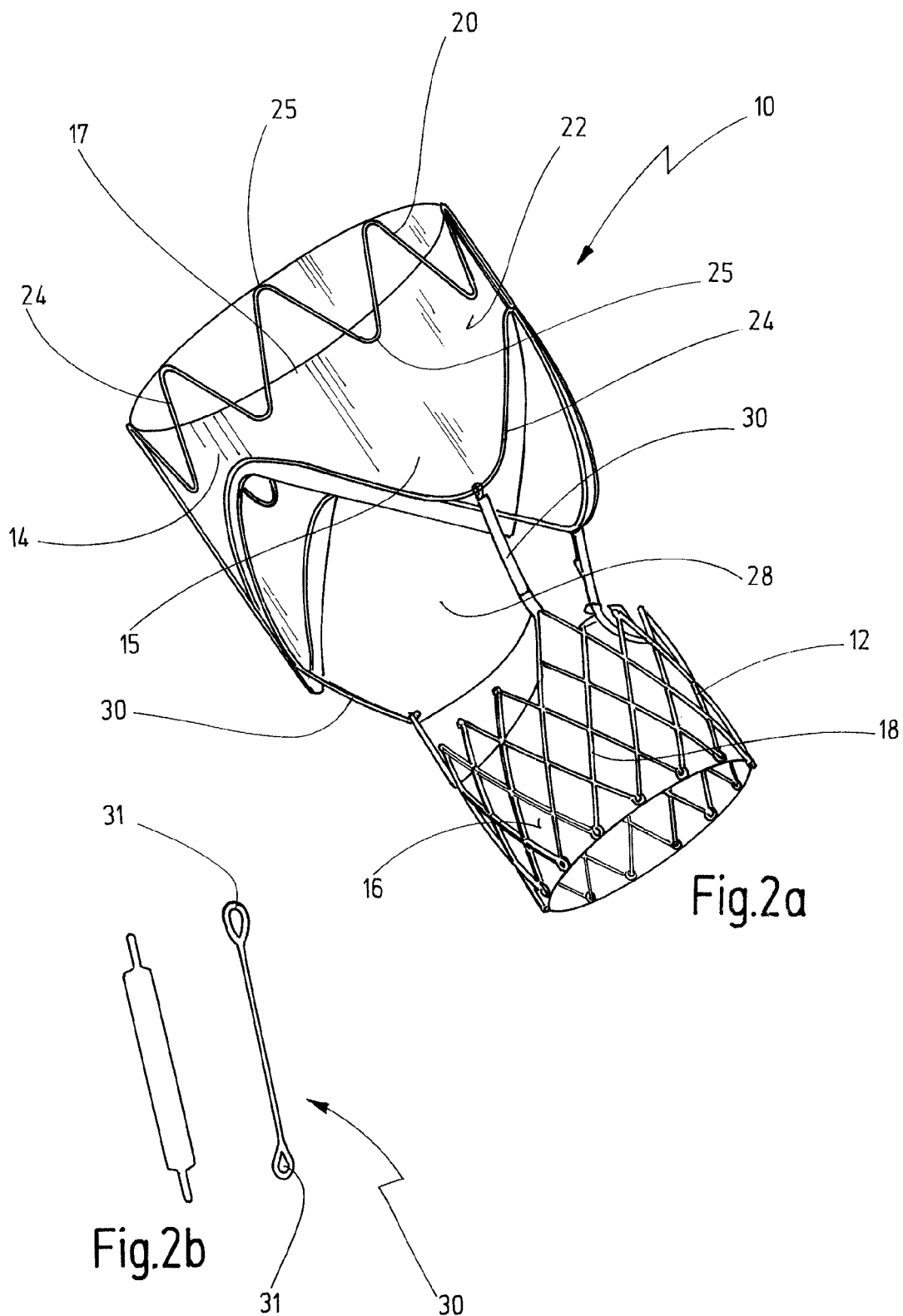

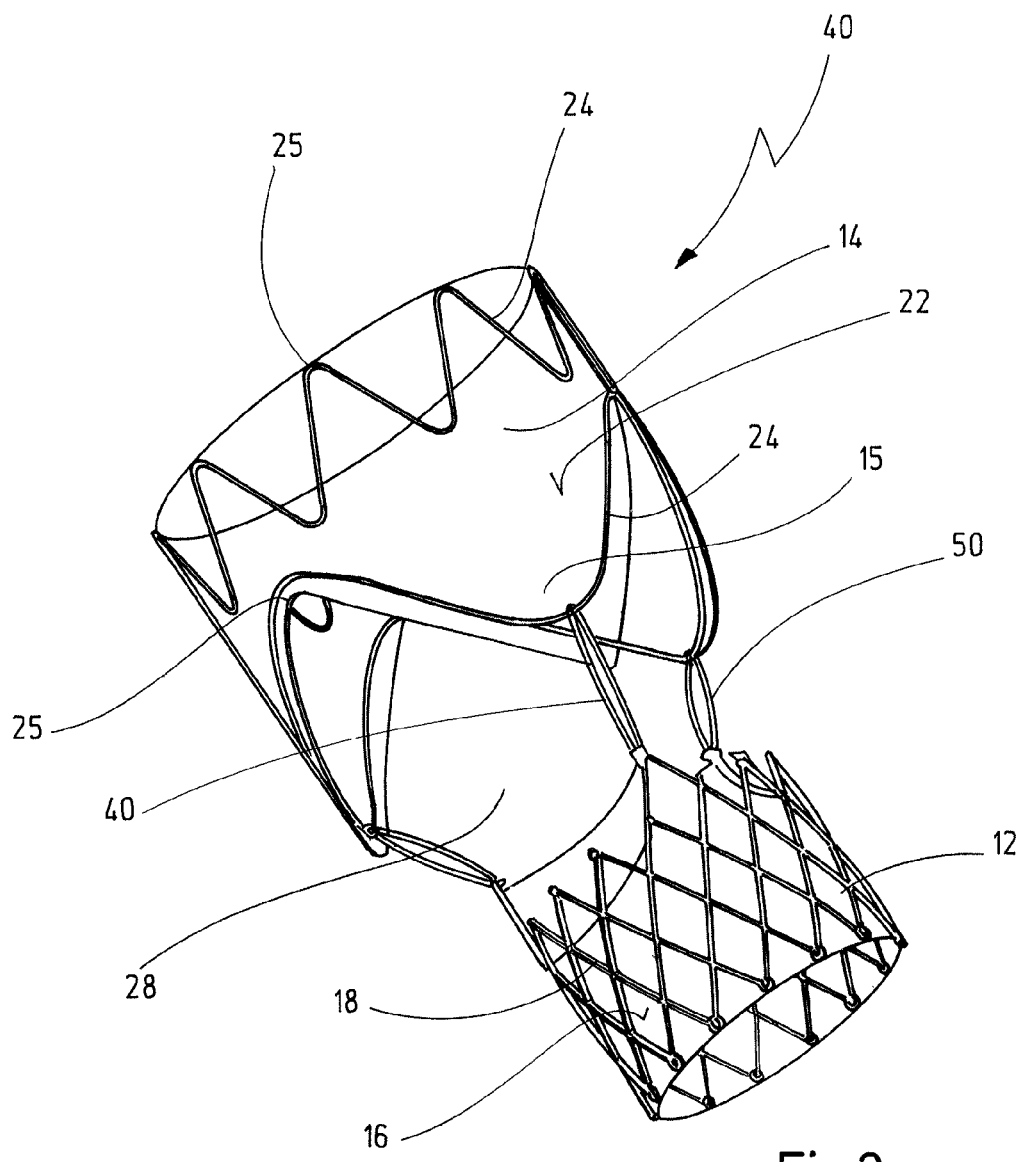
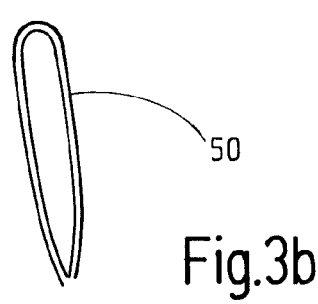
Fig.3a
Fig.3b

CARDIAC VALVE PROSTHESIS SYSTEM

CROSS REFERENCES TO RELATED APPLICATIONS

This application is a continuation of international patent application PCT/EP2008/005868, filed on Jul. 17, 2008, designating the U.S., which international patent application has been published in English language, and which entire content is incorporated herein by reference.

BACKGROUND OF THE INVENTION

The present invention relates to a cardiac valve prosthesis system for implantation into the body of a mammal, comprising a valve mounted on a stent element to form a stented valve element, and an anchoring element to be arranged within the aorta and spaced-apart form the stented valve element.

Valve prosthesis systems of this kind are usually used for replacing damaged, mal- or nonfunctioning cardiac valves. In the heart, cardiac valves maintain the unidirectional flow of blood by opening and closing depending on the difference in pressure on each side.

Besides the valve of the coronary sinus and the valve of the inferior vena cava, there are four valves of the heart: The two atrioventricular (AV) valves, which ensure blood flows from the atria to the ventricles, and not the other way, and the two semilunar (SL) vales, which are present in the arteries leaving the heart—i.e. on the pulmonary artery and the aorta—and which prevent blood flowing back from the arteries into the ventricles. The aortic valve, one of the semilunar valves, lies between the left ventricle and the aorta. The heart valves, except for the mitral valve, consist of three cusps or flaps which serve to seal the heart valves when closed.

The aortic valve can be affected by a range of diseases and can, therefore, require aortic valve replacement, which means that a patient's aortic valve is replaced by a different valve. The valve can either become leaky, i.e. regurgitant or insufficient, in which case the aortic valve is incompetent and blood flows passively back to the heart in the wrong direction. Further, the valve can become partially shut, i.e. stenotic, in which case the valve fails to open fully, thereby obstructing blood flow out from the heart. The two conditions frequently co-exist.

Aortic valve replacement traditionally requires median sternotomy and thus open heart surgery, which is a major impact on the patient to be treated: The chestbone is sawed in half and after opening of the pericardium, the patient is placed on a cardiopulmonary bypass machine. Once the patient is on bypass, the patient's diseased aortic valve is removed and a mechanical or tissue valve is put in its place. Besides the physical stress associated with this operation, there is a risk of death or serious complications from open heart surgery, in particular depending on the health and age of the patient.

However, recently, valves are developed that can be implanted using a catheter with out open heart surgery.

There are two basic types of artificial heart valve, mechanical valves and tissue valves. Tissue heart valves are usually made from animal tissues, either animal heart valve tissue or animal pericardial tissue, which are treated to prevent rejection and to prevent calcification. Whereas mechanical valves generally are designed to outlast the patient, they have the drawback that due to their material there is an increased risk of blood clots forming, which may only be prevented by a constant anti-coagulant therapy, which makes the patient more prone to bleeding. Mechanical heart valves are generally composed entirely of synthetic or nonbiological materials, whereas tissue (or bioprosthetic) heart valves are composed of synthetic and biological materials. Bioprosthetic cardiac valves can either represent xenografts, which are taken from different species than the recipient, or homografts, which are donor valves taken from the same species as the recipient.

EP 0 592 419 describes a cardiac vale prosthesis comprising a collapsible elastical valve which is mounted on an elastical/self-expanding stent. The commissural points of the elastical valve are mounted on the cylinder surface of the elastical/self-expanding stent, which is made from a radially collapsible and re-expandable cylindrical support element. The prosthesis is implanted in the body by means of catheterization.

Further, U.S. Pat. No. 6,652,578 discloses a prosthetic cardiac valve stent consisting of an expandable stent body member and a graft member, wherein the latter is made of biologically-derived membranes or biocompatible synthetic materials.

Nevertheless, a major disadvantage of the valves of the state of the art is their insufficient capability to be securely anchored in place of the valve to be replaced with the artificial valve. Further, many cardiac valve replacement devices do not comprise an element by means of which the artificial valve can be sufficiently secured to the place of the natural valve that is intended to be replaced. Thus, with such cardiac valves of the state of the art there is the danger of the valve migrating into the vessel and thereby not fulfilling the requirements of a replacement valve any longer.

On the other hand, in order to provide for an secure anchoring of the valve replacement device in a vessel, some of the cardiac valve replacements known in the state of the art represent stiff and bulky devices which is why such cardiac valve replacements often lead to vessel anatomy modifications and consequently to valve malfunctions.

In view of the above, an object of the present invention is to provide a new cardiac valve prosthesis system that overcomes the drawbacks of the prior art and which allows for a secure anchoring of the valve replacement device without the danger of blocking or obstructing the blood flow into adjacent vessels.

SUMMARY OF THE INVENTION

This and other objects are achieved by a cardiac valve prosthesis system as mentioned at the outset, wherein the anchoring element comprises a cylindrical tube element composed of fabric supported by a metal mesh, and wherein the stented valve element and the anchoring element represent two constructional distinctive elements being associated by ligament-like connecting means, such, that a connecting region between the stented valve element and the anchoring element is generally free from foreign material.

With the cardiac valve replacement system according to the invention it is thus possible to securely anchor the system in a vessel of a patient: The stented valve element of the replacement system, which is supposed to replace the affected native valve, is deployed over said native valve, e.g. by compressing the valve element inside a catheter and releasing it over the valve to be replaced. At the same time, the anchoring element of the replacement system, which is associated with the valve element by connecting means, is deployed in the aorta adjacent to the valve element thereby securely anchoring the valve element at the place of the native valve and the system in the vessel.

Further, with the connecting region between the stented valve element and the anchoring element being generally free from foreign material, the perfusion of vessels laying above the valve, in particular the coronary arteries is ensured.

After deployment, the anchoring element, which is, e.g., to be placed in the lower portion of the ascending aorta expands, such, that it securely lies against the vessel wall thereby anchoring its cylindrical tube composed of fabric supported by a metal mesh in the aorta. Due to the fact that the valve element and the anchoring element are spaced apart by the connecting means, such, that a connecting region is formed which is generally free from material, vessels branching off in the area of the lower portion of the ascending aorta and in the area of the cardiac valve can still be supplied with blood.

Within the scope of the present invention, the term "generally free from material" is supposed to mean, that besides the ligament-like connecting means no other material is provided to connect the valve element and the anchoring element, such, that areas are formed between the valve element and the anchoring element that are free from any material, and that form quasi free openings in the replacement system.

Further, the term "ligament-like" is presently supposed to mean any form of a connection means between the valve element and the anchoring element, that comprises or has a band-, strand-, ligament-, or bar-like, or similar, form, and that therefore represents a fine or slight connection element between said two elements free from any covering.

The expression "anchoring element" is supposed to mean any element being designed such, that by its abutting to the vessel walls the system is securely held in place of its deployment site.

The expression "spaced apart" is supposed to mean, that the anchoring element and the valve element do not directly abut on one another, but are separated. In the context of the present invention, said two elements of the replacement system are spaced apart—and thus separated—by the connecting means.

A "stent" is generally understood as a radially expandable endoprosthesis representing a typical intravascular implant which is implanted by a transluminal route and which is enlarged radially or expanded after it has been introduced. Stents can be self-expanding or are expanded by a radial force applied from inside, for example if they are fitted on a balloon.

In a preferred embodiment of the invention the ligament-like connecting means of the cardiac valve prosthesis system comprise suturing or mechanical means, by which the stented valve element is connected with the anchoring element.

With the connecting means comprising or being suturing or mechanical means, the two elements, i.e. the stented valve element and the anchoring element can effectively and conveniently be connected, whilst remaining spaced-apart and leaving a connecting region in between, which is generally free from material. In the context of the present invention, the term "suturing means" generally implies materials that are non-rigid, but rather flexible filaments or fibers.

In this connection, it is preferred, if said suturing means are thread-like structures. Under "thread-like structures", threads, filaments, or fibers, or the like are meant, which are suited to provide for a suture connection of the two elements of the valve prosthesis. E.g., a biocompatible thread of a certain length may be used to connect the two elements, whilst providing a certain distance between said two elements, thus generating the connecting region generally free of material.

In particular, the threads or suturing means used in connection with the present invention as connecting means can be suturing means like threads that are currently used in medicine, e.g. for surgical sutures, and that are biocompatible and consist of a natural or synthetic material. Exemplary materials that may be used as suturing means are polypropylene, polyester, polyethylene terephthalate, polybutylene terephthalate, polyamide, nylons, or Goretex®, or stainless steel, NITINOL or any other metal alloy. In principle, any biocompatible, nonabsorbable suturing means can be used that has proven to be suitable for implantable medical devices or are highly likely to be suitable.

According to another preferred embodiment of the invention, said ligament-like connecting means comprise flexible bar-formed structures which, via their ends, are associated with said stented valve element and said anchoring element respectively.

Within the context of the present invention, the term "bar-formed", is supposed to mean any element that forms a rigid usually straight length of any material, that is suitable for implanting into a human body, and that may be, e.g. metal, etc. "Bar-formed" may further mean a narrow band or stripe made from a rather rigid material, such as, e.g. metal.

Using a bar-formed and rather rigid connecting means of a certain length, this allows to keep the two elements, i.e. the stented valve element and the anchoring element spaced apart, such, that an connecting region is formed, which is generally free from material. It is to be understood, that any material that fulfils the requirements of the above definition of "bar-formed" connecting means may be used, as long as it is biocompatible.

Further, the suturing means allows to individually determining the distance between the two elements of the valve prosthesis, which means that the prosthesis may be custom-made in view of the patient to be treated. This has a particular advantage, since the individual conditions of a heart, valve, and aorta, and of the vessels branching off can be quite differing from patient to patient.

In a refinement of the invention, the stented valve element is associated with the anchoring element via three poles of the valve.

Generally, a natural aortic valve contains three leaflets, or cusps, poles, or flaps of connective tissue that passively move apart or mate together in response to the forces imposed by the flow of blood. Accordingly, with the term "poles of the valve" three alignments are meant, with 120 degrees apart from one another in the circumferential edge of the stent, where the commissure of the valve leaflets are sutured to.

In a refinement of the invention, it is preferred if said metal mesh of the cylindrical tube element of the anchoring element consists of at least two metal rings meandering circumferentially and which are disposed successively in the anchoring element's longitudinal direction, and that the fabric of the cylindrical tube element consists of a fabric material which is fixed to the rings and which connects them, said fabric material forming a hollow cylindrical body. Thereby, the rings are merely connected via the fabric material, and are not interconnected directly with one another, i.e. the rings do not touch or cross each other, or are otherwise directly connected or bound to one another.

This embodiment has the advantage that preformed stent or stent graft elements may be used as anchoring element in the valve prosthesis system. Such stent elements or stent graft element are known in the state of the art and are, e.g. described in German Patent Application DE 100 65 824.5, the content of which is herewith explicitly referred to.

In this connection, it is preferred if the metal rings have a Z-shaped profile with pointed arches pointing alternately toward the proximal end and distal end of the anchoring element.

In a refinement of the invention, it is preferred if the number of pointed arches of the last ring of the proximal end of the anchoring element is smaller than the number of pointed arches of the rings that are disposed successively to the last ring toward the distal end of the anchoring element.

In particular, it is preferred if the last ring of the proximal end comprises three pointed arches pointing toward the proximal end of the anchoring element, and, in particular, if the three poles of the stented valve element, via the connecting means, are associated with said three pointed arches.

In a preferred embodiment of the invention, the stent element of the stented valve element is a self-expanding stent element. In particular, it is preferred if the stent element of the stented valve element comprises a shape-memory material, including at least one of a shape-memory polymer or a shape-memory metal, in particular nitinol.

Such self-expanding stent elements contain an elastic material which can expand outwards, i.e. radially, as soon as force exerted to compress the material for introducing the stent element into a vessel, e.g. a sleeve, is removed. Preferably, nitinol is used, which can also have shape-memory properties, for this purpose. The framework of the stent is made of this material and preferably has a tubular structure, which usually has a slightly larger diameter than the vessel into which it is to be implanted. The advantage of this measure is that because of its superelasticity, the stent automatically resumes its original shape after release from a compressed state used for introducing the prosthesis.

Similarly, it is further preferred, if the metal mesh of the anchoring element consists of rings comprising a shape-memory material, including at least one of a shape-memory polymer or a shape-memory metal, in particular nitinol.

In another preferred embodiment of the invention, the fabric of the anchoring element comprises a material selected form the group polymers, preferably polyester.

Such fabrics, used with stents to form stent grafts, are generally known in the state of the art, and may comprise any natural or synthetic polymer that is biocompatible and suitable as a "jacket" for the stent framework within the context of the present invention. Further, the polymers may be coated with a medically active substance or any other substance to influence and/or treat a condition of a patient at the site of implantation of the prosthesis. This measure is known per se, and the medically active substances can, for example, prevent stenosis, accelerate healing of wounds of the inside wall of the vessel, or prevent the development of inflammations. In addition, the mesh of the anchoring element and/or the stented valve element may be coated or treated with medically active substance.

In a refinement of the invention, it is preferred, if the valve is a heart valve comprising a material selected from the group human, bovine, porcine, or equine pericardium tissue. Thus, the valve may be either a xenograft or a homograft. It is particularly preferred if said material is treated, e.g., with glutaraldehyde. The biocompatible material to be used as valve replacement is usually fabricated by fixing said material in glutaraldehyde solution, which functions as a tissue preservative. Although fixation in glutaraldehyde may imply drawbacks in view of biomaterial calcification, glutaraldehyde fixation still remains the method of choice for preserving tissue and preparing it for implantation as a biomaterial. In this connection, it is preferred if the valve prosthesis is treated with a substance that prevents calcification, e.g. with dimethyl sulfoxide, or similar.

The present invention further concerns a process for producing a cardiac valve prosthesis as disclosed therein, the process comprising the following steps:

providing a valve mounted on a stent element to form a stented valve element, providing an anchoring element comprising a cylindrical tube element composed of fabric supported by a metal mesh, and connecting the stented valve element and the anchoring element by ligament-like connecting means, such, that a connecting region between the stented valve element and the anchoring element is formed, which is generally free from foreign material.

In particular, it is preferred if the ligament-like connecting means used for connecting the stented valve element and the anchoring element are suturing and/or mechanical means.

The valve prosthesis according to the invention will be placed in the heart using an endovascular catheter. The delivery site may be reached in three different ways:

Via transfemoral, i.e. in a retrograded fashion, using a long catheter accessing the femoral artery, iliac artery and aorta and deploying the stented valve element over the native leaflets and, subsequently, the deploying the anchoring element in the ascending aorta.

Via transapical, i.e. in a anterograded fashion, with a medium size catheter accessing with small thoracotomy and puncture in the apex of the left ventricle of the heart and deploying first the anchoring element in the ascending aorta and subsequently the stented valve element over the original valve or in the opposite way, deploying first the stented valve and subsequently the anchoring element.

Finally, in an open heart surgery with a cardiopulmonary bypass; in doing so, the aorta root is dissected, the original leaflets of the valve are collected, i.e. cut out, and subsequently the valve prosthesis is placed directly in the annulus by means of a short flexible catheter and suturing the stent graft to the ascending aorta. However, the latter way, is—due to the drawbacks mentioned at the outset—the least preferable; nevertheless, there might be certain circumstances where such an operation might be necessary.

It will be appreciated, that the above-mentioned features, which are discussed in more detail below, can be used not only in the combination respectively cited, but also alone or in other combinations, without departing from the scope of the present invention.

BRIEF DESCRIPTION OF THE DRAWINGS

The invention is described in more detail by the description and figures below. They show:

FIG. 2a a perspective schematic drawing of an embodiment of the valve prosthesis according to the invention;

FIG. 2b an enlarged view of the connecting means of the valve prosthesis shown in FIG. 1a;

FIG. 3a a perspective schematic drawing of another embodiment of the valve prosthesis according to the invention; and FIG. 3b an enlarged view of the connecting means of the valve prosthesis shown in FIG. 2a.

DESCRIPTION OF PREFERRED EMBODIMENTS

Figure 1:
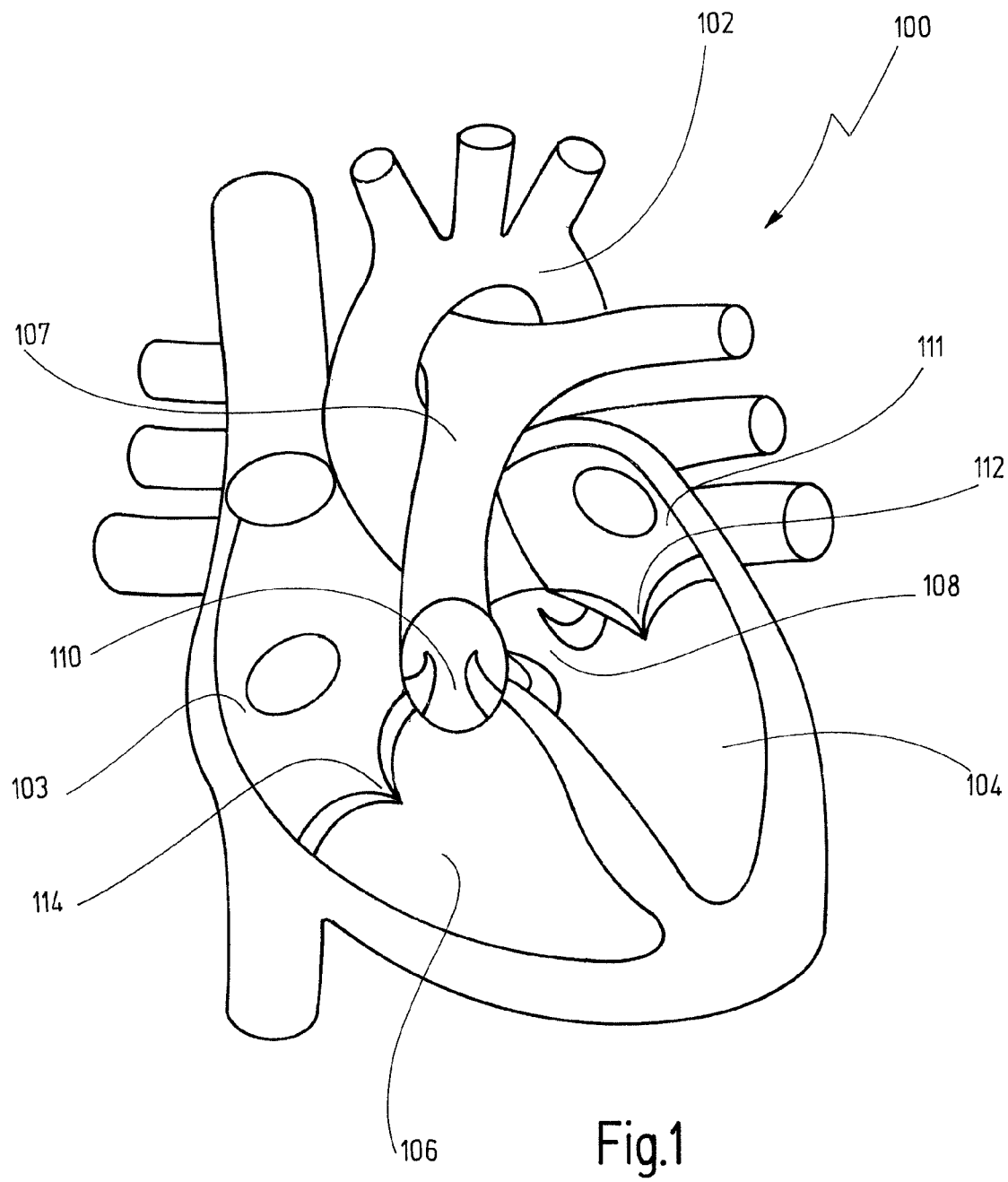
FIG. 1 a schematic drawing of the heart.

In FIG. 1, reference number 100 designates a human heart, with the aorta indicated with 102, the left ventricle with 104 and the right ventricle with 106. The four valves of the heart 100 are the aortic valve 108, lying between the left ventricle 104 and the aorta 102, the pulmonic valve 110, lying between the right ventricle 106 and the pulmonary artery 107, the mitral valve 112, lying between the left ventricle 104 and the left atrium 111, and the tricuspid valve 114, lying between the right atrium 113 and the right ventricle 106.

When during ventricular systole the pressure in the left ventricle 104 rises above the pressure in the aorta 102, the aortic valve 108 opens, allowing blood to exit the left ventricle 104 into the aorta 102. When ventricular systole ends, pressure in the left ventricle 104 rapidly decreases, whereby the aortic pressure forces the aortic valve 108 to close.

In patients with a diseased and/or malfunctioning aortic valve 108, the valve 108 has to be replaced with a valve prosthesis.

In FIG. 2a, reference sign 10 designates a cardiac prosthesis comprising a stented valve element 12 and an anchoring element 14. The stented valve element 12 comprises a valve material 16, preferably consisting of a human, bovine, porcine or equine pericardium tissue. The valve material 16 is sutured inside a cylindrical stent 18. The stent is preferable self expandable and represents a highly elastic metal stent, preferably made from laser cut nitinol.

In the shown embodiment, the anchoring element 14 represents stent graft, which comprises a cylindrical stent 20 and a graft 22. The graft 22 fixedly covers the stent 20 on its outside, like an envelope or a mantle. The graft 22 is preferably made of a natural of synthetic polymer. The stent is made of a metal springs, preferable of nitinol. The springs represent two metal rings 24 meandering circumferentially and are disposed successively in the anchoring element's 14 longitudinal direction. The graft 22 or fabric of the cylindrical stent is fixed to the rings and connects them.

Further, as can be seen from FIG. 2a, the metal rings 24 have a Z-shaped profile with pointed arches 25 pointing alternately toward the proximal end 15 and distal end 17 of the anchoring element 14.

In FIG. 2a, connecting means 30 are shown, connecting the anchoring element 14 with the stented valve element 12. The connecting means 30 are also shown in FIG. 2b, in an enlarged view. In the embodiment depicted in FIG. 2, the connecting means 30 show a bar-formed design: They represent rods having a loop 31 on each end, as can be seen in FIG. 2b. The bar-formed connecting means can be made of, e.g., any metal that is biocompatible with the human body. As shown in FIG. 2a, the connecting means 30, or rather their loops 31 connect—on the one side—with the metal ring 24 of the anchoring element 14; in particular, they connect with the very metal ring 24 of the anchoring element 14, which is positioned—with respect to the further rings 24 of the anchoring element—proximate to the stented valve element 12, even more precisely at the arches 25 of said metal ring 24, which are pointing in the direction of the stented valve element 12. With their other side, or rather with the loop provided at this side, the connecting means are connected with the stent portion of the stented valve element to the stented valve pole at its top, linked trough a physical element as i.e. a hole at the pole. By varying the length of the connecting means 30, the anchoring element 14 and the valve element 12 are spaced apart, thereby forming an connecting region 28 between the stented valve element 12 and the anchoring element 14, the region 28 of which is generally free from foreign material, in particular free from material 16 or 22.

Further, as can be seen from FIG. 2a, the anchoring element 14, via the connecting means 30, is associated via its proximal end 15 with the stented valve element 12, wherein only the pointed arches 25 of the last ring 24 of the proximal end 15 pointing toward the proximal end 15 of the anchoring element 14 are covered by the graft 22 or fabric material 22. Due to the meandering last ring 24 and due to the last ring 24 pointing away from the proximal end 15 of the anchoring element 14, areas are formed that are not covered by the graft or fabric material 22.

Further, as can be also taken from FIG. 2a, the number of pointed arches 25 of the last ring 24 of the proximal end 15 of the anchoring element 14 is smaller than the number of pointed arches 25 of the rings 24 that are disposed successively to the last ring 24 toward the distal end 17 of the anchoring element 14, and, in particular, that the last ring 24 of the proximal end 15 comprises three pointed arches 25 pointing toward the proximal end 14 of the anchoring element 14.

Referring now to FIG. 3, the same features of this embodiment are designated with the same reference numbers as the corresponding features of the embodiment depicted in FIG. 2. Thus, also the embodiment of the valve prosthesis 40 shown in FIG. 3a comprises an anchoring element 14 and a valve element 12, both elements being connected by connecting means 50. The design of the anchoring element 14 and of the stented valve element 12 corresponds to the anchoring element 14 and to the stented valve element of FIG. 2a, respectively. In short, the stented valve element 12 comprises a valve material 16, which is sutured inside a cylindrical, preferably self-expanding stent 18, preferably made from laser cut nitinol.

Further, in the embodiment shown in FIG. 3a, the anchoring element 14 represents stent graft, which comprises a cylindrical stent 20 comprising springs and a graft 22, which fixedly covers the stent 20 on its outside. The springs represent two metal rings 24 meandering circumferentially. The graft 22 or fabric of the cylindrical stent is fixed to the rings and connects them.

In FIG. 3a, connecting means 50 are shown, connecting the anchoring element 14 with the stented valve element 12. The connecting means 50 are also shown in FIG. 3b, in an enlarged view. In the embodiment depicted in FIG. 3, the connecting means 50 are three suturing means in the form filaments or fibres having a thread-like structure. The three threads are guided through the stent arches 25 of the anchoring element and are sutured to the poles of the valve 16 of the valve element 12. Due to the length of the threads, the anchoring element 14 and the valve element 12 are spaced apart. Further, a connecting region 28 is formed between the stented valve element 12 and the anchoring element 14, the region of which is generally free from foreign material, in particular free from material 16 or 22.

Thus, with the valve prosthesis exemplary shown in the embodiments of FIGS. 2 and 3, the connecting region remains free from any foreign material, thereby ensuring that coronary perfusion. This is due to the fact that the connecting region will be placed within the coronaries ostium area, so that blood flow into these vessels is not obstructed by the valve prosthesis material.

What is claimed is:

1. A cardiac valve prosthesis system for implantation into the body of a mammal, comprising
 a valve mounted on a stent element to form a stented valve element and
 an anchoring element to be arranged within the aorta of the mammal and spaced-apart distally from the stented valve element, wherein the anchoring element comprises a cylindrical tube element composed of fabric supported by a metal mesh consisting of two or more metal rings, meandering circumferentially and being disposed successively in the anchoring element's longitudinal direction, wherein the metal rings have a Z-shaped profile with pointed arches pointing alternately toward the proximal end and distal end of the anchoring element, wherein the stented valve element and the anchoring element represent two constructional distinctive elements being associated only by ligament-like connecting means, such that the stented valve element and the anchoring element are spaced-apart and do not directly contact each other, and wherein said fabric of the cylindrical tube element consists of a fabric material which is fixed to the rings thereby connecting them, wherein said rings are connected to each other only by said fabric material, and wherein said rings do not touch or cross each other, said fabric material forming a hollow cylindrical body, and wherein the last ring of the anchoring element has only three pointed arches pointing toward the proximal end of the anchoring element, and wherein the stented valve element is associated with the anchoring element via three poles of the valve, the three poles of the valve, via the connecting means, being associated with said three pointed arches.

2. The cardiac valve prosthesis system according to claim 1, wherein the ligament-like connecting means comprise suturing or mechanical means, by which the stented valve element is connected with the anchoring element.

3. The cardiac valve prosthesis system according to claim 1, wherein the ligament-like connecting means comprise suturing means consisting of thread-like structures.

4. The cardiac valve prosthesis system according to claim 1, wherein said ligament-like connecting means comprise flexible bar-formed structures which, via their ends, are associated with said stented valve element and said anchoring element respectively.

5. The cardiac valve prosthesis system according to claim 1, wherein the number of pointed arches of the last ring of the proximal end of the anchoring element is smaller than the number of pointed arches of the rings that are disposed successively to the last ring toward the distal end of the anchoring element.

6. The cardiac valve prosthesis system according to claim 1, wherein the stent element of the stented valve element is a self-expanding stent element.

7. The cardiac valve prosthesis system according to claim 1, wherein the stent element of the stented valve element comprises a shape-memory material, including at least one of a shape-memory polymer or a shape-memory metal.

8. The cardiac valve prosthesis system according to claim 1, wherein the fabric of the anchoring element comprises a material selected from the group polymers.

9. The cardiac valve prosthesis system according to claim 1, wherein the metal mesh of the anchoring element consists of rings comprising a shape-memory material, including at least one of a shape-memory polymer or a shape-memory metal.

10. The cardiac valve prosthesis system according to claim 1, wherein the valve is a heart valve comprising a material selected from the group human, bovine, porcine, or equine pericardium tissue.

11. A process for producing a cardiac valve prosthesis of claim 1, the process comprising the following steps:

providing a valve mounted on a stent element to form a stented valve element, providing an anchoring element to be arranged in the aorta of a patient comprising a cylindrical tube element composed of fabric supported by a metal mesh, said metal mesh consisting of two or more metal rings, meandering circumferentially and being disposed successively in the anchoring element's longitudinal direction, wherein the metal rings have a Z-shaped profile with pointed arches pointing alternately toward the proximal end and distal end of the anchoring element, wherein the last ring of the proximal end has only three pointed arches pointing toward the proximal end of the anchoring element, and said fabric of the cylindrical tube element consisting of a fabric material which is fixed to the rings thereby connecting them, wherein said fabric of the cylindrical tube element consists of a fabric material which is fixed to the rings thereby connecting them, wherein said rings are connected to each other only by said fabric material, and wherein said rings do not touch or cross each other, said fabric material forming a hollow cylindrical body, and said fabric material forming a hollow cylindrical body, and connecting the stented valve element and the anchoring element by ligament-like connecting means, such that the stented valve element and the anchoring element are spaced-apart and do not directly contact each other, and that the stented valve element is associated with the anchoring element via three poles of the valve.

12. The process of claim 11, wherein the ligament-like connecting means used for connecting the stented valve element and the anchoring element are suturing and/or mechanical means.

13. The cardiac valve prosthesis system according to claim 1, wherein the stent element of the stented valve element comprises nitinol.

14. The cardiac valve prosthesis system according to claim 1, wherein the fabric of the anchoring element comprises polyester.

15. The cardiac valve prosthesis system according to claim 1, wherein the metal mesh of the anchoring element consists of rings comprising nitinol.

* * * * *